United States Patent [19]

Seppelt et al.

[11] Patent Number: 4,880,837
[45] Date of Patent: Nov. 14, 1989

[54] N-BENZOYL-N'-(2,3-DICHLORO-4-PHENOXY)-PHENYLUREAS

[75] Inventors: Wolfgang Seppelt, Bobenheim-Roxheim; Peter Hofmeister, Neustadt; Christoph Kuenast, Otterstadt, all of Fed. Rep. of Germany

[73] Assignee: BASF Aktiengesellschaft, Ludwigshafen, Fed. Rep. of Germany

[21] Appl. No.: 246,268

[22] Filed: Sep. 19, 1988

[30] Foreign Application Priority Data

Sep. 19, 1987 [DE] Fed. Rep. of Germany ....... 3731561

[51] Int. Cl.⁴ ................... A01N 47/28; A01N 25/00; C07C 127/22
[52] U.S. Cl. .................................... 514/594; 564/44; 424/405
[58] Field of Search .......... 424/405; 514/594; 71/88; 564/44

[56] References Cited

U.S. PATENT DOCUMENTS 4,567,295 1/1986 Brouwer et al. .................. 514/594
4,656,193 4/1987 Brouwer et al. .................. 514/594

FOREIGN PATENT DOCUMENTS 0101990 6/1983 European Pat. Off. .
2531202 1/1978 Fed. Rep. of Germany .
3232265 3/1984 Fed. Rep. of Germany .
3309987 9/1984 Fed. Rep. of Germany .

Primary Examiner—Thurman K. Page
Assistant Examiner—Penny L. Prater
Attorney, Agent, or Firm—Oblon, Spivak, McClelland, Maier & Neustadt

[57] ABSTRACT

N-Benzoyl-N'-(2,3-dichloro-4-phenoxy)-phenylureas of the general formula I where $R^1$ is halogen, $R^2$ is hydrogen or halogen, $R^3$ is halogen or $C_1$-$C_4$-haloalkoxy, and $R^4$ is hydrogen or halogen, pesticides containing compounds I as active ingredients, and methods of combating pests.

4 Claims, No Drawings

N-BENZOYL-N'-(2,3-DICHLORO-4-PHENOXY)-PHENYLUREAS

The present invention relates to novel N-benzoyl-N'-(2,3-dichloro-4-phenoxy)-phenylureas of the general formula I

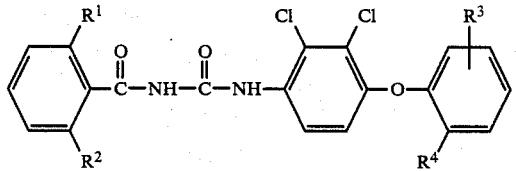

where $R^1$ is halogen, $R^2$ is hydrogen or halogen, $R^3$ is halogen or $C_1$–$C_4$-haloalkoxy and $R^4$ is hydrogen or halogen.

The present invention furthermore relates to the preparation of the compounds I, pesticides which contain the compounds I as active ingredients and a method for controlling pests.

DE-A-25 31 202, DE-A-32 32 265 and DE-A-33 09 987 disclose N-benzoyl-N'-phenoxyphenylureas for controlling pests, although the said compounds are not chlorinated in the 2,3-position in the N-phenyl moiety. The prior art compounds have an unsatisfactory action.

It is an object of the present invention to provide novel urea derivatives having an improved action.

We have found that this object is achieved by the novel N-benzoyl-N'-(2,3-dichloro-4-phenoxy)-phenylureas I defined at the outset, processes for their preparation, pesticides which contain the compounds I as active ingredients, and a method for controlling pests with N-benzoyl-N'-(2,3-dichloro-4-phenoxy)-phenylureas I.

The compounds I are obtainable by the following methods:

(a) by reacting a benzoyl isocyanate of the general formula II

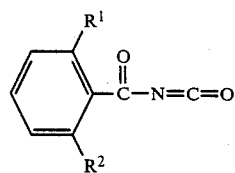

with a (2,3-dichloro-4-phenoxy)-aniline of the general formula III

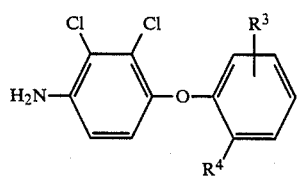

or (b) by reacting a benzamide of the general formula IV

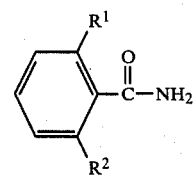

with a (2,3-dichloro-4-phenoxy)-phenyl isocyanate of the general formula V

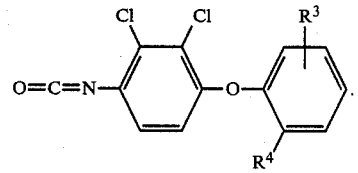

Reaction (a) is carried out at from 0° to 120° C., preferably from 20° to 80° C., particularly preferably from 20° to 60° C., and under from 1 to 10 bar, preferably under atmospheric pressure. Since the reaction takes place with evolution of heat (exothermic), it may be advantageous to provide a means of cooling.

Advantageously, the (2,3-diochloro-4-phenoxy)aniline of the formula III is initially taken in a solvent or diluent, and the benzoyl isocyanate of the formula II is then added. The reaction is generally complete after 2 hours.

The benzoylisocyanates II are known or can be prepared by known methods (J. Org. Chem. 28 (1963), 1805–1811 or J. Agr. Chem. 21 (1973), 3488 et seq. The (2,3-dichloro-4-phenoxy)-anilines III are likewise known or can be prepared by known methods (Houben/Weyl, Methoden der Organischen Chemie, Vol. XI/1, 360 et seq. (1975). The parent nitrobenzenes and their preparation are known from Barry et al., Pr. Irish Acad. 53B (1950), 6166–6182.

Reaction (b) is carried out in the presence or absence of a catalyst, at from 0° to 140° C., preferably from 60° to 100° C., and under from 1 to 10 bar, preferably atmospheric pressure. The reaction time is in general from 2 to 6 hours.

Examples of suitable catalysts are organic bases, such as triethylamine, pyridine, 4-N-N-dimethylaminopyridine and alkali metal compounds, such as dibutyltin diacetate.

The benzamides IV are known or are obtainable by known methods (eg. Houben-Weyl, Methoden der organischen Chemie, Vol. E 5.2, page 934 et seq, Georg-Thieme Verlag, 1985). Some of the (2,3-dichloro-4-phenoxy)-phenyl isocyanates V are known; those which are unknown can be obtained by conventional methods (eg. Houben-Weyl, Methoden der organischen Chemie, Vol. E 4, page 738 et seq., Georg-Thieme Verlag, 1983).

The starting materials II and III or IV and V are usually used in a stoichiometric ratio. However, an excess of one or other of the components may be quite advantageous in specific cases.

The reactions (a) and (b) (cf. also DE-A-21 23 236) are advantageously carried out in a solvent or diluent. For example, the following are suitable for this purpose: aliphatic and aromatic hydrocarbons and chlorohydrocarbons, such as petroleum ether, benzene, toluene, xylene, gasoline, dichloromethane, chloroform, tetrachloromethane, 1,2-dichloromethane and chlorobenzene, ethers and esters, such as diethyl and di-n-butyl ether, methyl tert-butyl ether, tetrahydrofuran, dioxane and ethyl acetate, ketones, eg. acetone, methyl ethyl ketone and methyl isopropyl ketone, nitriles, such as acetonitrile and propionitrile, and aprotic dipolar solvents, such as dimethylformamide, dimethyl sulfoxide and pyridine. Mixtures of these substances can also be used as solvents or diluents.

Some of the novel compounds of the formula I are obtained in the form of oils, which can be freed from the final volatile constituents by prolonged heating to moderately elevated temperatures under reduced pressure (incipient distillation) and can be purified in this manner. If the compounds of the formula I are obtained in crystalline form, they can be purified by recrystallization.

The substituents in formula I have the following specific meanings: $R^1$ is halogen, such as fluorine, chlorine, bromine or iodine, preferably fluorine or chlorine, $R^2$ is hydrogen or halogen, such as fluorine, chlorine, bromine or iodine, preferably fluorine or chlorine, $R^3$ is halogen, preferably fluorine, chlorine or bromine, $C_1$–$C_4$-haloalkoxy, preferably $C_1$- or $C_2$-fluoro- or chloroalkoxy, particularly preferably fluorine-substituted and chlorine-substituted methoxy, or fluoromethoxy, difluoromethoxy, trifluoromethoxy, chloromethoxy, dichloromethoxy, trichloromethoxy, chlorofluoromethoxy, dichlorofluoromethoxy or chlorodifluoromethoxy, and $R^4$ is hydrogen or halogen, preferably fluorine, chlorine or bromine.

The N-benzoyl-N'-(2,3-dichloro-4-phenoxy)-phenylureas of the general formula I are suitable for effectively controlling pests from the class consisting of the insects, arachnida and nematodes. They can be used as pesticides in crop protection, in the hygiene and veterinary sectors and for protecting stored materials.

In contrast to most of the conventional active ingredients, which are contact or ingested poisons and kill, incapacitate or repel the animals, the compounds of the formula I interfere with the development of the animal organism. In the case of insects, for example, the transformation to the imago, the laying of viable eggs and the development of normal laid eggs are disturbed and the sequence of generations thus interrupted. The novel active ingredients are virtually completely non-toxic to vertebrates. Moreover, the compounds of the formula I are readily degraded to form substances which occur in the natural environment and are further decomposed by microorganisms. There is therefore no danger of accumulation. Accordingly, they can safely be used for controlling pests in animals, crops and stored materials.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebra, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephela, Cheimatobia brumata, Hibernia defoliaria, Bupalus pinarius, Hyphantria cunea, Agrotis segetum, Agrotis ypsilon, Barathra brassicae, Cirphis unipuncta, Prodenia litura, Laphygma exigua, Panolis flammea, Earis insulana, Plusia gamma, Alabama argillacea, Lymantria dispar, Lymantria monacha,* and *Pieris brassicae;* examples from the Coleoptera order are *Blitophaga undata, Melanotus communis, Limonius californicus, Agriotes lineatus, Agriotes obscurus, Agrilus sinuatus, Meligethes aeneus, Atomaria linearis, Epilachna varicestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus pacificus, Paratetranychus pilosus, Bryobia praetiosa, Ixodes ricinus, Ornithodorus moubata, Amblyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes e.g., *Heterodera rostochiensis, Heterodera schach-* tii, Heterodera avenae, Heterodera glycines, and Heterodera trifolii, and stem and leaf eelworms, e.g., Ditylenchus dipsaci, Ditylenchus destructor, Pratylenchus neglectus, Pratylenchus penetrans, Pratylenchus goodeyi, Pratylenchus curvitatus and Tylenchorhynchus dubius, Tylenchorhynchus claytoni, Rotylenchus robusttus, Heliocotylenchus multicinctus, Radopholus similis, Belonolaimus longicaudatus, Longidorus elongatus, and Trichodorus primitivus.

The active ingredients may be applied for instances as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol gylcol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 1 is intimately mixed with 95 parts by weight of particulate kaolin. A dust is obtained containing 5% by weight of the active ingredient.

II. 30 parts by weight of compound no. 7 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 11 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 17 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 18 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The active ingredient concentrations in the finished formulations may vary over a wide range. Generally, they are from 0.0001 to 10, and preferably from 0.01 to 1, %. The active ingredients may also successfully be used in the ultra-low-volume (ULV) method, where it is possible to apply formulations containing more than 95wt% of active ingredient, or even the active ingredient without additives.

In the open, the amount of active ingredient applied is for example from 0.001 to 10, and preferably from 0.02 to 2, kg/ha.

There may be added to the active ingredients (if desired, immediately before use (tankmix) oils of various types, herbicides, fungicides, other insecticides and bactericides. These agents may be added to the active ingredients according to the invention in a weight ratio of from 1:10 to 10:1.

MANUFACTURING EXAMPLE

N-2,6-difluorobenzoyl-N'-2,3-dichloro-4-(4-bromo-2-fluorophenoxy)-phenylurea (compound no. 17)

21 g (0.11 mol) of 2,3,4-trichloronitrobenzene, 21.5 g (0.11 mol) of 4-bromo-2-fluorophenol and 31 g of K₂CO₃ are stirred in 150 ml of dimethylformamide for 24 hours at 120° C. The mixture is filtered after cooling and the solvent is distilled off under reduced pressure. There is obtained 41 g (97%) of an oily crude product which is further processed direct.

38 g (0.1 mol) of this 2,3-dichloro-4-(4-bromo-2-fluorophenoxy)-aniline is hydrogenated for 5 hours under a pressure of 10 bar in 300 ml of tetrahydrofuran in the presence of 4 g of Raney nickel. After the catalyst has been filtered off and the solvent distilled off, there remains 35 g (99%) of solidified product.

At room temperature, 3.7 g (0.02 mole) of 2,6-difluorobenzoyl isocyanate is dripped into 7 g (0.02 mol) of 2,3-dichloro-4-(4-bromo-2-fluorophenoxy)aniline in 40 ml of tetrahydrofuran. This mixture is then stirred for 3 hours at 45° C. After removal of the solvent under reduced pressure, the residue is taken up in ligroin and suction filtered. There is obtained 7.9 g (74%) of N-2,6-difluorobenzoyl-N′-2,3-dichloro-4-(4-bromo-2-fluorophenoxy)-phenylurea (compound no. 17); m.p.: 167° C.

The compounds I listed in the table below may be prepared from appropriate precursors by the process according to the invention; a similar action may be expected.

TABLE

| Compound no. | R¹ | R² | R³ | R⁴ | mp. [°C.] |
|---|---|---|---|---|---|
| 1 | F | F | 4-F | H | 175 |
| 2 | Cl | H | 4-F | H | 146 |
| 3 | Cl | Cl | 4-F | H | |
| 4 | Cl | H | 4-Cl | H | |
| 5 | F | F | 4-Cl | Cl | |
| 6 | F | H | 4-F | H | 142 |
| 7 | F | F | 4-F | Cl | 151 |
| 8 | F | F | 4-Cl | H | |
| 9 | F | F | 4-Br | H | |
| 10 | F | F | 4-F | Br | 162 |
| 11 | F | F | 3-F | H | 182 |
| 12 | Cl | H | 3-F | H | 122 |
| 13 | Cl | H | 5-F | Cl | |
| 14 | Cl | H | 5-Cl | Cl | |
| 15 | F | F | 5-Cl | Cl | |
| 16 | Cl | H | 4-Br | F | 158 |
| 17 | F | F | 4-Br | F | 167 |
| 18 | F | F | 4-OCF₃ | H | 155 |
| 19 | Cl | H | 4-OCF₃ | H | 161 |

TABLE-continued

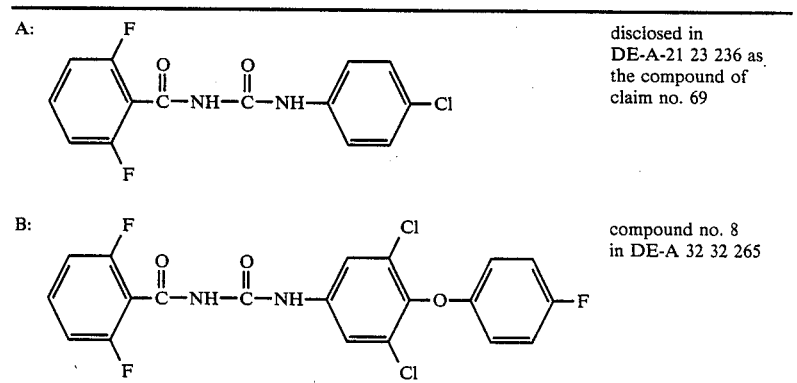

| Compound no. | R¹ | R² | R³ | R⁴ | mp. [°C.] |
|---|---|---|---|---|---|
| 20 | Cl | H | 4-OCF₃ | Cl | |

USE EXAMPLES

In the following examples, the action of compounds according to the invention, or agents containing them, on pests is compared with that of the following art compounds:

A: disclosed in DE-A-21 23 236 as the compound of claim no. 69

B: compound no. 8 in DE-A 32 32 265

The concentrations at which the candidate compounds exhibit 100% kill or inhibition are the minimum concentrations. The purity of comparative compounds A and B differed in no essential respect from that of the compounds according to the invention and was in each instance more than 95%.

EXAMPLE A

Breeding experiment with *Aedes aegypti* (yellow fever mosquito)

At 25° C., active ingredient formulations were added to 200 ml of tapwater in 250 ml plastic beakers. 20 to 30 mosquito larvae in the third to fourth larval stage were then introduced. The observation period covered pupation and hatching of the imagoes, which took place after 10 to 12 days. During this period a commercially available, powdered tropical fish food (Tetramin ®) was proffered once.

In this experiment, the lethal dose of compounds nos. 11, 17 and 18 was 0.002 ppm; the lethal dose of comparative compound A was 0.004 ppm. Comparative compound B achieved 100% kill at 0.04 ppm, whereas compound 1 (structurally closest) gave 100% kill at 0.004 ppm.

EXAMPLE B

*Musca domestica* (housefly); breeding experiment

The vessels employed were 50 ml penicillin jars, into which 4.75 ml of a nutrient slurry was introduced and to which 0.25 ml of aqueous active ingredient formulations was added.

About 10,000 one day old flies' eggs were suspended in about 100 ml of tapwater. A pipette was used to transfer one drop from this suspension into a jar.

The jar was stoppered with absorbent cotton and stored at 23° to 24° C. Evaluation took place on the fifth day.

In this experiment, compound no. 1 exhibited a kill rate of 80% at a concentration of 1 ppm, whereas comparative agent B had no effect at this rate and only achieved 100% kill at twice this concentration.

EXAMPLE C

Inhibition of the development of *Heliothis virescens* on treated nutrient medium 100 g of the standard nutrient medium for *Heliothis virescens* was filled into 250 ml beakers and carefully mixed, while warm, with aqueous formulations of the active ingredients. After the medium had cooled, 10 caterpillars of the third larval stage (1.5 to 1.8 cm) were introduced into each vessel, and the vessels were stored at 23° C. Pupation and hatching of the moths were assessed.

In this experiment, compound no. 11 achieved 80% kill at a rate of 0.1 ppm, compound no. 17 gave 90% kill at 0.1 ppm, and comparative compound A exhibited 90% kill at a rate of 4 ppm.

EXAMPLE D

Inhibition of the development of *Agrotis ypsilon* on a treated nutrient medium 100 g of the standard nutrient medium for Agrotis was filled into 250 ml beakers and carefully mixed, while warm, with aqueous formulations of the active ingredients. After the medium has cooled, 10 caterpillars of the third larval stage (1.5 to 1.8 cm) were introduced into each vessel, and the vessels were stored at 23° C. Pupation and hatching of the moths were assessed. Two beakers with a total of 20 caterpillars were used for each concentration.

In this experiment, the lethal dose of compounds nos. 7, 11, 17 and 18 was 0.1 ppm. Compound no. 19 (1 ppm) and compound no. 1 (4 ppm) achieved a kill of 90%. Comparative compound A exhibited a kill rate of 80% at a rate of 10 ppm.

EXAMPLE E

Breeding experiment with *Dysdercus intermedius* (cotton stainer)

1 ml of acetonic solutions of the active ingredients were used to line Petri dishes 10 cm in diameter. After the solvent had evaporated, 20 larvae of the penultimate stage were placed in the dishes. After 24 hours the survivors were transferred to 1 liter jars containing 200 g of sterile quartz sand (particle size: 0 to 3 mm). This sand had been watered prior to the experiment with 25 ml of aqueous formulations of the active ingredients. The food proffered was swollen cotton seeds which were replaced once a week. The sand was also moistened once a week with pure water.

The temperature was kept at 25° to 27° C. The jars were monitored until the eggs in the controls hatched. The kill rate was assessed.

In this experiment, compound no. 1 and comparative compound B achieved 100% kill at a rate of 4 ppm.

EXAMPLE F

Breeding experiment with *Ostrinia nubilalis* (corn borer)

Breeding took place on a culture medium made up of 515 g of cornflour, 130 g of wheat germ, 137 g of brewer's yeast, 18 g of ascorbic acid, 10 g of cellulose powder, 5 g of Nipagin, 20 g of Wessons salt, 20 ml of vitamin solution, 80 g of agar, and 3,100 of water. 50 ml of this medium is introduced into 100 ml plastic beakers, and the aqueous active ingredient formulations are carefully admixed.

After the vessels had cooled, 4 caterpillars (L 3) were introduced into each vessel. Five vessels were used for each concentration.

Monitoring was continued until the moths hatched.

In this experiment, compound no. 1 achieved 100% kill at a concentration of 20 ppm, whereas comparative compound B had no effect (0% kill) at this concentration.

We claim:

1. N-Benzoyl-N'-(2,3-dichloro-4-phenoxy)-phenylureas of the general formula I

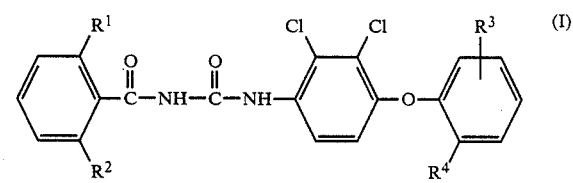

where $R^1$ is halogen, $R^2$ is hydrogen or halogen, $R^3$ is halogen or $C_1$-$C_4$-haloalkoxy, and $R^4$ is hydrogen or halogen.

2. N-Benzoyl-N'-(2,3-dichloro-4-phenoxy)-phenylureas of the formula I as set forth in claim 1, where $R^1$ is fluorine or chlorine, $R^2$ is hydrogen, fluorine or chlorine, $R^3$ is fluorine, chlorine, bromine or trifluoromethoxy, and $R^4$ is hydrogen, fluorine, chlorine or bromine.

3. A pesticide containing a pesticidally effective amount of an N-benzoyl-N'-(2,3-dichloro-4-phenoxy)-phenylurea of the formula I as set forth in claim 1 and solid or liquid carriers.

4. A pesticide as set forth in claim 3, containing from 0.1 to 95wt% of an N-benzoyl-N'-(2,3-dichloro-4-phenoxy)-phenylurea I.

* * * * *